United States Patent [19]

Schouteeten et al.

[11] 4,339,602

[45] Jul. 13, 1982

[54] PROCESS OF PREPARATION OF RACEMIC HYDROXYARYLGLYCOLIC ACIDS AND NOVEL PRODUCTS RESULTING THEREFROM

[75] Inventors: Alain Schouteeten, Ezanville; Yani Christidis, Paris, both of France

[73] Assignee: Societe Francaise Hoechst, France

[21] Appl. No.: 243,965

[22] PCT Filed: Jul. 24, 1980

[86] PCT No.: PCT/FR80/00126

§ 371 Date: Feb. 25, 1981

§ 102(e) Date: Feb. 25, 1981

[87] PCT Pub. No.: WO81/00254

PCT Pub. Date: Feb. 5, 1981

[30] Foreign Application Priority Data

Jul. 25, 1979 [FR] France .............................. 79 19171

[51] Int. Cl.³ ...................... C07C 65/11; C07C 59/50
[52] U.S. Cl. .................................... 562/466; 562/470
[58] Field of Search ................................ 562/470, 466

[56] References Cited

FOREIGN PATENT DOCUMENTS

2379501 9/1978 France .............................. 562/470
54-4003034 1/1979 Japan ................................ 562/470
55-5102537 8/1980 Japan ................................ 562/470

OTHER PUBLICATIONS

Chem. Abst. 91:193005r, vol. 91, 1979.
Chem. Abst. 92:22263g, vol. 92, 1979.

*Primary Examiner*—Paul J. Killos
*Attorney, Agent, or Firm*—Karl W. Flocks; Sheridan Neimark

[57] ABSTRACT

The invention relates to a process of preparation of racemic hydroxyarylglycolic acids and the novel products resulting therefrom.

According to such process glyoxylic acid is condensed in water in the presence of an alkaline agent at a temperature of between 35° and 100° C., on an excess, or not, of phenolic aromative derivative other than phenol, having at least one proton on either of the ortho or para positions with respect to the phenol function.

Application to the production of novel acids such as 4-hydroxy 3-tertiobutyl mandelic acid, 2-hydroxy 5-tertiobutyl mandelic acid, 3-chloro 4-hydroxy mandelic acid, 2-fluoro 4-hydroxy mandelic acid, monohydrated 3,5-dimethoxy 4-hydroxy mandelic acid, 2-hydroxy 5-methyl mandelic acid, (1-hydroxy 2-naphthyl) glycolic acid, 4-ethyl 2-hydroxy mandelic acid, and 4-hydroxy 3-methyl mandelic acid.

1 Claim, No Drawings

PROCESS OF PREPARATION OF RACEMIC HYDROXYARYLGLYCOLIC ACIDS AND NOVEL PRODUCTS RESULTING THEREFROM

This invention relates to a novel process of preparation of racemic ortho- or parahydroxyarylglycolic acids and novel products resulting therefrom.

Racemic hydroxyarylglycolic acids are raw materials appreciated in organic synthesis, since the works of P. Hebert, Bull. Soc. Chim. France, 1920, 27 (4th series), 45-55, have confirmed their degradation into carbonylated derivative by decarboxylating oxidation.

It is known from the prior art to accede to racemic hydroxyarylglycolic acids from an aromatic phenol derivative in alkaline aqueous medium either by condensation of glyoxylic acid in accordance with U.S. Pat. No. 2,062,205 or by condensation of chloral followed by a hydrolysis of the hydroxyaryltrichloromethylcarbinol, formed according to Austrian Pat. No. 141 159.

It is known that glyoxylic acid in alkaline aqueous medium is little stable and dismutes when hot quantitatively into oxalic and glycolic acids by Cannizzaro's reaction (BOETTINGER, Ber., 1880, 13 1931I). For this reason, reactions that involve glyoxylic acid in alkaline aqueous medium are achieved at a temperature lower or equal to the room temperature. Thus, in the process described in French Pat. No. 2,132,364, condensation of glyoxylic acid with phenol in excess dissolved in 10% aqueous sodium hydroxide solution is achieved at 15° to 25° C. in 36 hours. In German Pat. No. 621 567, an alkaline aqueous solution of phenol and glyoxylic acid is held several days at the room temperature to obtain racemic parahydroxymandelic acid. J. GOODMAN et Al., Biochem. Biophys. Acta, 1968, 156, 364.67, condense glyoxylic acid with gaiacol in 68 hours at 25° C., and J. KAMLET, U.S. Pat. No. 2,640,083 proceeds in 48 hours at 15°-20° C. to prepare racemic 4-hydroxy 3-methoxy mandelic acid. Recently, Belgian Pat. No. 867 287 has described a process for obtaining an alkaline metal salt of solid monohydrated parahydroxymandelic acid by condensing glyoxylic acid with phenol in excess in alkaline aqueous solution at a temperature slightly higher than room temperature either in 18 hours from 30° to 35° C. (example 1) or 5 hours at 35° C. (example 2), or again 8 hours at 35° C. (example 3).

According to A. I. FATIADI et R. SCHAFFER, J. Research Nat. Bur. Stand., Sect. A, 1972, 78A, 411-12, any increase in temperature affects negatively the condensation yield of glyoxylic acid on gaiacol to accede to racemic 4-hydroxy 3-methoxy mandelic acid, and these authors recommend carrying out such condensation by supplying glyoxylic acid in 4 hours into an alkaline aqueous solution of gaiacol, cooled to about 0° C., and then maintaining the reaction medium for 20 hours at 0°-20° C. For the preparation of racemic 3,4-dihydroxy mandelic acid NIPPON SYNTHETIC CHEMICAL INDUSTRY Co. Ltd. in their Japanese patent application No. 75-29522 (C.A. Vol. 83 58435a) teaches to react glyoxylic acid with pyrocatechol in 2 hours at 5°-8° C., then in 24 hours at 10°-15° C. and finally 24 hours at room temperature.

The Applicant in his French patent application No. 78-31123 claims a process for preparing racemic parahydroxy mandelic acid by condensation of glyoxylic acid with phenol in excess, in water in the presence of an alkaline agent, at a temperature between 30° and 100° C.

The Applicant has now found that glyoxylic acid condenses quickly in alkaline aqueous medium at a temperature between 35°-50° and 100° C., advantageously between 50° and 100° C., and even better between 50° and 85° C., with an excess or not of an aromatic phenol derivative other than phenol, having at least one nuclear proton in the ortho or para position with respect to the hydroxy phenolic group, to produce a racemic ortho- or parahydroxyarylglycolic acid. This condensation is not site selective in view of resonance of phenolate anion communicating some carbanion nature to the ortho and para positions. Notwithstanding the lack of site selectiveness of such condensation, it generally provides predominantly the para isomer with respect to the phenolic group, except if this position is either already substituted as in the case of the para-substituted phenols, or hindered by the presence of a bulk group on one of the meta-sites of the starting phenol as in the case of 3-ethyl phenol or again deactivated by electronic effects from various substituents of the starting phenol.

The percentage of isomers present at the end of the treatment in the crude reaction product can be found either by nuclear magnetic resonance spectroscopy of the proton or by potentiometric analysis in a nonaqueous medium by means of tetrabutylammonium hydroxide. As a matter of fact, in NMR the methine proton in the benzyl position of the ortho-hydroxyaryl glycolic acids resonates at lower fields than its homologous of the para-hydroxyaryl glycolic acids. By dosage of the carboxylic function in a non aqueous medium it is generally observed that ortho-hydroxyarylglycolic acids are more acid than the corresponding para-isomers. Moreover, by dosage in an aqueous medium of the phenol function it can be noted in many cases that it cannot be measured when it is on the ortho-position of the 2-hydroxy acetic side chain.

The aromatic phenolic derivatives useful as starting materials are for example gaiacol, 2-ethoxy phenol (guethol), pyrocatechol, ortho-cresol, para-cresol, ortho-tertiobutylphenol, para-tertiobutylphenol, or-tho-chlorophenol, meta-ethylphenol, meta-fluorophenol, 2,6-dimethoxy phenol, beta-naphthol and the like.

According to the invention glyoxylic acid is condensed in an alkaline aqueous medium at a temperature from 50° to 100° C., advantageously from 50° to 85° C., with an excess or not of aromatic phenol derivative for several tens of minutes, then after neutralization of the reaction medium at pH in the order of 6.5, the unconverted phenol derivative is removed by extraction with a water-immiscible or water-little miscible organic solvent, then the aqueous phase is acidified at pH in the order of 0.5, and the desired product is extracted with a water-immiscible or water-little miscible solvent. Thus, after elimination of the extraction solvent and re-crystallization of the residue, the desired pure racemic ortho- or parahydroxyarylglycolic acid is isolated.

More precisely, one mole 50% glyoxyl acid is condensed for several tens of minutes between 50° and 100° C., advantageously for 45 minutes between 50° and 85° C., in a nitrogen atmosphere with 1 to 4 moles, preferably, 2 to 3 moles, and especially, 3 moles of aromatic phenol derivative other than phenol, having at least one nuclear proton in the ortho or para position with respect to the hydroxyphenol group in solution in 1 to 4 liters of water containing 2-4 moles of sodium hydroxide, preferably, 2 to 3 liters of water containing 2-3 moles of sodium hydroxide and advantageously in 1.8 liters of water containing 2.25 mol. of sodium hydroxide, then the reaction medium is neutralized at pH=6.5 with concentrated hydrochloric acid, then the starting aromatic phenol derivative not transformed is extracted by ethyl acetate, finally after acidification of the aqueous phase, at a pH of 0.5, with concentrated hydrochloric acid, the desired racemic ortho- and/or parahydroxyarylglycolic acid(s) is(are) extracted by ethyl acetate. Thus, after evaporation of the extraction solvent, a crystallized residue is isolated; it is either the desired crude racemic ortho- or parahydroxyarylglycolic acid or a mixture of isomers of crude racemic ortho- and parahydroxyarylglycolic acids. These crude product or mixture submitted to re-crystallization provide pure racemic ortho- or parahydroxyarylglycolic acid the structure of which is determined by nuclear magnetic resonance spectroscopy of the proton at 60 MHz in solution either in dimethylsulfoxide $d_6$ or acetone $d_6$.

The following examples are given in a purely illustrative way and do not limit the invention thereto.

EXAMPLE 1

A solution obtained by dissolving the following is heated for 45 minutes from 35° to 85° C. with agitation in a nitrogen atmosphere:
 1.5 moles (186.2 g) of gaiacol;
 0.5 mole (74 g) of 50% glyoxylic acid in water;
 1.125 moles (45 g) of sodium hydroxide in pellets in 900 g of water.

After cooling from 85° to 30° C., in 20 minutes, the reaction medium is acidified at a pH of 6.5 with concentrated hydrochloric acid (d=1.18) then unconverted gaiacol is extracted by ethyl acetate. Thus, 1.04 moles (129.1 g) of gaiacol is isolated after removal of the extraction solvent. The residual aqueous phase acidified thereafter at a pH=0.5 with concentrated hydrochloric acid, is washed with ethyl acetate to extract the desired product.

After removal under vacuum of ethyl acetate, 80 g of crystallized product having an instantaneous melting point of 116° C. is collected; this product is re-crystallized in 10 volumes of nitromethane; after drying under vacuum at 80° C. at a constant weight, 66.3 g (0.33 mole) of racemic 4-hydroxy 3-methoxy mandelic acid are isolated, having a melting point of 132°±1° C., i.e. a yield of 66% with respect to the glyoxylic acid used (In the literature: melting point=133° C., J. A. F. GARDNER et Al., J. Amer. Chem. Soc., 1944, 66, 607).

NMR (acetone $d_6$)
 $\delta$=3.75 ppm s 3 H (OCH$_3$)
 $\delta$=5.05 ppm s 1 H (H benzylic)
 $\delta$=6.65–7.05 ppm m 3 H (H aromatic)

EXAMPLE 2

The procedure of example 1 is followed but gaiacol is replaced by 1.5 moles (207.2 g) of ortho-ethoxyphenol. At the end of treatment 142.3 g (1.03 moles) of ortho-ethoxyphenol is obtained and 83.5 g of crystallized product having a melting point of 121°±1° C. are collected. After re-crystallization in 7 volumes of nitromethane and drying under vacuum at 80° C. at a constant weight, 72.37 g (0.341 mole) of racemic 3-ethoxy 4-hydroxy mandelic acid are isolated, having a melting point of 126°±1° C., i.e. a yield of 68.2% with respect to the glyoxylic acid used (In the literature, melting point =104°–105° C., hydrate with 1 mole H$_2$O, P. P. SHORYGIN et Al.

Sintezy Dushistykh Veshchestv, Sbornik Staiei, 1939, 7–13; C.A. 42, 3267).

| Microanalysis. $C_{10}H_{12}O_5$ = 212.20 | | | |
|---|---|---|---|
| | C % | H % | O % |
| calculated | 56.60 | 5.70 | 37.70 |
| found | 56.20 | 5.6 | |

NMR (acetone $d_6$)
 $\delta$=1.33 ppm t 3 H (H methyl) J=7 Hz
 $\delta$=4.03 ppm q 2 H (H—OCH$_2$) J=7 Hz
 $\delta$=5.22 ppm s 1 H (H benzylic)
 $\delta$=6.6–6.8 ppm m 3 H (H aromatic)

EXAMPLE 3

The procedure of example 1 is followed, but gaiacol is replaced by 1.5 moles (165.2 g) of pyrocatechol. At the end of treatment 1.02 moles (112.3 g) of unreacted pyrocatechol is recovered and 88.2 g of crystallized product having a melting point of 124° C. is collected. After re-crystallization in 30 volumes of nitromethane and drying under vacuum at 80° C. at a constant weight, 52.9 g (0.287 moles) of racemic 3,4-dihydroxy mandelic acid is isolated having a melting point of 138°±1° C. i.e. a yield of 57.4% with respect to glyoxylic acid used (In the literature: melting point=137° C., K. N. F. Shaw et Al., J. Org. Chem. 1958, 23, 31).

NMR (acetone $d_6$)
 $\delta$=4.93 ppm s 1 H (H benzylic)
 $\delta$=6.7–6.8 ppm m 3 H (aromatic)

EXAMPLE 4

The procedure according to example 1 is followed but gaiacol is replaced by 1.5 moles (162.2 g) of ortho-cresol. At the end of treatment, 0.97 moles (105 g) of unreacted ortho-cresol is obtained and 120 g of crystallized product having a melting point of 105° C. is collected. After re-crystallization in 120 volumes of dichloroethane, and drying in vacuum at 80° C. at a constant weight, 68 g (0.373 moles) of 4-hydroxy 3-methyl mandelic acid is isolated having a melting point of 114°±1° C. i.e. a yield of 74.6% with respect to glyoxylic acid used.

| Microanalysis $C_9H_{10}O_4$ = 182.17 | | | |
|---|---|---|---|
| | C % | H % | O % |
| calculated | 59.33 | 5.53 | 35.13 |
| found | 59.2 | 5.5 | |

NMR of the proton (acetone $d_6$)
 $\delta$=2.15 ppm s, 3 H (CH$_3$)
 $\delta$=5.05 ppm s, 1 H (H benzylic)
 $\delta$=6.55–7.15 ppm m, 3 H (aromatic)

To the Applicant's knowledge this product has not been described in the literature. The 4-hydroxy 3-methyl mandelic acid has been cited in the literature: P. KOHLER et H. BAUFELD, Aerztlolal, 1964, IO (7), 224–25, C.A. 1964, 61, 16415a, but examination of this publication shows that it is the 3-methoxy 4-hydroxy mandelic acid, thereby confirming the summary made by the authors at the end of the paper.

EXAMPLE 5

The procedure of example 1 is followed but gaiacol is replaced by 1.5 moles (225.3 g) of ortho-tertiobutyl-phenol. At the end of treatment 1.29 moles of unreacted ortho-tertiobutylphenol is recovered and 21.3 g of crystallized product is collected, providing after re-crystallization in 4 volumes of nitromethane and drying in vacuum at 80° C. at a constant weight, 12.8 g (0.057 moles) of racemic 4-hydroxy 3-tertiobutyl mandelic acid having a melting point of 158°±1° C., i.e. a yield of 11.5% with respect to glyoxylic acid used.

Potentiometric dosage carboxylic function 4.44 meq/g (theory: 4.46 meq/g)

NMR (acetone $d_6$)

$\delta = 1.4$ ppm s 9 H (tert.Bu)
$\delta = 5.08$ ppm s 1 H (benzylic)
$\delta = 6.7$ ppm d 1 H ($H_5$ aromatic) J $H_5$-$H_6$ = 8 Hz
$\delta = 7.12$ ppm q 1 H ($H_6$ aromatic) J $H_6$-$H_5$ = 8 Hz J $H_6$ $H_2$ = 2 Hz
$\delta = 7.4$ ppm d 1 H ($H_2$ aromatic) J $H_2$-$H_6$ = 2 Hz To the Applicant's knowledge, this product has not been described in the literature.

EXAMPLE 6

The procedure of example 1 is followed but gaiacol is replaced by 1.5 moles (225.3 g) of para-tertiobutylphenol. At the end of treatment, 1.35 moles (202.8 g) of para-tertiobutylphenol is recovered and 28 g of crystallized product is collected, providing after re-crystallization in 3 volumes of 1,2-dichloroethane, 16.15 g (0.072 moles) of racemic 2-hydroxy 5-tertiobutyl mandelic acid having a melting point of 119°±1° C. i.e. a yield of 14.4% with respect to glyoxylic acid used.

| Microanalysis $C_{12}H_{16}O_4$ = 224.25 | | | |
|---|---|---|---|
| | C % | H % | O % |
| calculated | 64.27 | 7.19 | 28.54 |
| found | 64.3 | 7.15 | |

NMR (acetone $d_6$)

$\delta = 1.23$ ppm s 9 H (tertioBu)
$\delta = 5.38$ ppm s 1 H (H benzylic)
$\delta = 6.7$ ppm d 1 H ($H_3$ aromatic) J $H_3$ $H_4$ = 8.5 Hz
$\delta = 7.13$ ppm q 1 H ($H_4$ aromatic) J $H_4$ $H_3$ = 8.5 $H_3$ J $H_4$ $H_6$ = 2 $H_3$
$\delta = 7.3$ ppm d 1 H ($H_6$ aromatic) J $H_6$ $H_4$ = 2 Hz To the Applicant's knowledge, this product has not been described in the literature.

EXAMPLE 7

The procedure of example 1 is followed but gaiacol is replaced by 1.5 moles (192.8 g) of ortho-chlorophenol. At the end of treatment, 1.07 moles (137.6 g) of unreacted ortho-chlorophenol is recovered and 82.4 g of crystallized product (m.p. = 130°-138° C.) is collected, providing after recrystallization in 10 volumes of nitromethane and drying at constant weight under vacuum at 80° C., 68.2 g (0.337 moles) of racemic 3-chloro 4-hydroxy mandelic acid having a m.p. of 146°±1° C., i.e. a yield of 67.4% with respect to glyoxylic acid used.

| Microanalysis $C_8H_7ClO_4$ = 202.6 | | | | |
|---|---|---|---|---|
| | C % | H % | Cl % | O % |
| calculated | 47.42 | 3.48 | 17.50 | 31,59 |
| found | 47.6 | 3.6 | 17.4 | |

NMR (acetone $d_6$)

$\delta = 5.13$ ppm s 1 H (H benzylic)

$\delta = 6.93$ ppm d 1 H ($H_5$ aromatic) J $H_5$ $H_6$ = 9 Hz
$\delta = 7.27$ ppm q 1 H ($H_6$ aromatic) J $H_6$ $H_5$ = 9 Hz J $H_6$ $H_2$ = 2 Hz
$\delta = 7.43$ ppm d 1 H ($H_2$ aromatic) J $H_2$ $H_6$ = 2 Hz To the Applicant's knowledge, this product has never been described in the literature.

EXAMPLE 8

The procedure of example 1 is followed but gaiacol is replaced by 1.5 moles (186.2 g) of monomethyl ether of (para-methoxyphenol) hydroquinone. At the end of treatment 1.09 moles (135.3 g) of monomethyl ether of the unreacted hydroquinone is recovered and 81 g of crystallized product, m.p. = 129°±1° C., providing after re-crystallization in 10 volumes of nitromethane and drying at 80° C. under vacuum at constant weight, 65.6 g (0.331 moles) of racemic 2-hydroxy 5-methoxy mandelic acid having a melting point of 135°-136° C., i.e. a yield of 66.2% with respect to the glyoxylic acid used. (m.p. = 135° C., Th. Koppe and Witoszynskyi, Arch. Pharm., 1975, 308,344).

| Microanalysis $C_9H_{10}O_5$ = 198.17 | | | |
|---|---|---|---|
| | C % | H % | O % |
| calculated | 54,54 | 5,08 | 40,37 |
| found | 54,6 | 5,05 | |

NMR (dimethylsulfoxide $d_6$)

$\delta = 3.6$ ppm s 3 H (-$OCH_3$)
$\delta = 5.18$ ppm s 1 H (H benzylic)
$\delta = 6.6$-6.8 ppm m 3 H (H aromatic)

EXAMPLE 9

The procedure of example 1 is followed but gaiacol is replaced by 1.5 moles (162.2 g) of para-cresol. At the end of treatment, 1.12 moles (121.1 g) of unreacted para-cresol is recovered and 78 g of crystallized product is collected, providing after re-crystallization in 2 volumes of nitromethane and drying under vacuum at constant weight at 80° C., 42.5 g (0.233 mole) of racemic 2-hydroxy 5-methyl mandelic acid having a m.p. of 104°±1° C., i.e. a yield of 46.6% with respect to the glyoxylic acid used.

| Microanalysis $C_9H_{10}O_4$ = 182.17 | | | |
|---|---|---|---|
| | C % | H % | O % |
| calculated | 59.33 | 5.53 | 35.13 |
| found | 59.3 | 5.6 | |

NMR of proton (acetone $d_6$)

$\delta = 2.18$ ppm s 3 H ($CH_3$)
$\delta = 5.37$ ppm s 1 H (H benzylic)
$\delta = 6.65$ ppm d 1 H ($H_3$ aromatic) J $H_3$ $H_4$ = 8 Hz
$\delta = 6.9$ ppm q 1 H ($H_4$ aromatic) J $H_4$ $H_3$ = 8 Hz J $H_4$ $H_6$ = 1.5 Hz
$\delta = 7.03$ ppm d 1 H ($H_6$ aromatic) J $H_6$ $H_4$ = 1.5 Hz

| Dosage by potentiometry |
|---|
| Function phenol 5.44 meq/g |
| Function carboxyl 5.45 meq/g     (theory: 5.5 meq/g) |

To the Applicant's knowledge, this product has never been described in the literature. However, its potassium salt in aqueous solution was obtained intermediarily by F. BOEDECKER (German Pat. No. 621 567) during preparation of 2-hydroxy 5-methyl benzaldehyde from para-cresol.

EXAMPLE 10

The procedure of example 1 is followed but gaiacol is replaced by 1.5 moles (183.2 g) of meta-ethylphenol. At the end of treatment, 1.1 moles (134.4 g) of meta-ethylphenol is recovered and 95 g of crude product is collected. This crude product is analyzed by NMR of the porton in solution in deuterated dimethylsulfoxide and the signals from the proton in benzylic position are integrated. The spectra indicate that this crude product is constituted by 30% of racemic 2-ethyl 4-hydroxy mandelic acid, (para-isomer), (chemical displacement of benzylic proton delta=5 ppm), and by 70% of racemic 4-ethyl 2-hydroxy mandelic acid, (ortho-isomer), (chemical displacement of benzylic proton delta=5.15 ppm).

By re-crystallization in nitromethane, racemic 4-ethyl 2-hydroxy mandelic acid having a melting point =98°±2° C. is isolated.

| | Microanalysis $C_{10}H_{12}O_4 = 196.20$ | | |
|---|---|---|---|
| | C % | H % | O % |
| calculated | 61.21 | 6.17 | 32.62 |
| found | 61.4 | 6.1 | |

NMR (dimethylsulfoxide $d_6$)
$\delta=1.15$ ppm t 3 H ($CH_3$) J=7.5 Hz
$\delta=2.5$ ppm q 2 H ($CH_2$) J=7.5 Hz
$\delta=5.15$ ppm s 1 H (H benzylic)
$\delta=6.55$ ppm q 1 H (H5 aromatic) J $H_5 H_6=8$ Hz J $H_5 H_3=1$ Hz
$\delta=6.6$ ppm d 1 H (H3 aromatic) J $H_3 H_5=1$ Hz
$\delta=7.05$ ppm d 1 H (H6 aromatic) J $H_6 H_5=8$ Hz To the Applicant's knowledge, this product has never been known in the literature.

EXAMPLE 11

The procedure of example 1 is followed but gaiacol is replaced by 1.5 moles (168.15 g) of meta-fluorophenol. At the end of treatment, 1.03 moles (115.5 g) of meta-fluorophenol is recovered and 91 g of crystallized product, m.p.=127°±2° C., is collected, producing after re-crystallization in 5 volumes of nitromethane and drying at constant weight at 80° C. under vacuum, 62.5 g (0.336 moles) of racemic 2-fluoro 4-hydroxy mandelic acid having a m.p. of 144° C., i.e. a yield of 67.2% with respect to glyoxylic acid used.

| | Microanalysis $C_8H_7FO_4 = 186.14$ | | | |
|---|---|---|---|---|
| | C % | H % | F % | O % |
| calculated | 51.61 | 3.79 | 10.21 | 34.38 |
| found | 51.7 | 3.9 | | |

NMR (acetone $d_6$)
$\delta=5.3$ ppm s 1 H (H benzylic)
$\delta=6.47$ ppm q 1 H (H3 aromatic) J $H_3 F=10$ Hz J $H_3 H_5=2$ Hz
$\delta=6.57$ ppm sext. 1 H (H5 aromatic) J $H_5H_3=2$ Hz J $H_5 H_6=8$ Hz J $H_5 F=2$ Hz
$\delta=7.21$ ppm t 1 H (H6 aromatic) J $H_6H_5=8$ Hz J $H_6 F=8$ Hz To the Applicant's knowledge this product has not been described in the literature.

EXAMPLE 12

The procedure of example 1 is followed but gaiacol is replaced by 1.5 moles (231.2 g) of 2,6-dimethoxyphenol. At the end of treatment, 0.98 mole (151.1 g) of 2,6-dimethoxyphenol is recovered and 115 g of crystallized product is collected, m.p.=109° C., producing after re-crystallization in 5 volumes of ethyl acetate and drying under vacuum at 80° C. at constant weight, 91.26 g (0.37 mole) of racemic monohydrated 3,5-dimethoxy 4-hydroxy mandelic acid having a m.p.=109° C., i.e. a yield of 74% with respect to glyoxylic acid used.

| | Microanalysis $C_{10}H_{12}O_6, H_2O = 246.22$ | | | |
|---|---|---|---|---|
| | C % | H % | O % | $H_2O^+$ |
| calculated | 48.78 | 5.73 | 45.49 | 7.32 |
| found | 49.0 | 5.7 | | 7.1 |

+determined by K. Fischer's method.

NMR (acetone $d_6$)
$\delta=3.72$ ppm s 6 H ($OCH_3$)
$\delta=4.97$ ppm s 1 H (H benzylic)
$\delta=6.67$ ppm s 2 H (H aromatic)

To the Applicant's knowledge this product has not been described in the literature.

EXAMPLE 13

The procedure of example 1 is followed but gaiacol is replaced by 1.5 moles of β-naphthol (216.2 g). At the end of treatment, 1.1 moles (158.6 g) of β-naphthol is recovered and 91.5 g of crystallized product, m.p.=126° C., is collected, producing after re-crystallization in 7 volumes of nitromethane and drying at 80° C. under vacuum at constant weight, 24.2 g (0.111 mole) of racemic (1-hydroxy 2-naphthyl)glycolic acid having a m.p. of 126°±1° C., i.e. a yield of 22.2% with respect to glyoxylic acid used.

| | Microanalysis $C_{12}H_{10}O_4 = 218.20$ | | |
|---|---|---|---|
| | C % | H % | O % |
| calculated | 66.05 | 4.62 | 29.33 |
| found | 66.1 | 4.6 | |

NMR (dimethylsulfoxide $d_6$)
$\delta=5.9$ ppm s 1 H (H benzylic)
$\delta=6.98-8.1$ ppm m 6 H (aromatic)

To the Applicant's knowledge, this product has not been described in the literature.

It will be understood that this invention was only described in a purely explanative not limitative way and that any useful change can be brought thereto without departing from its scope as defined in the appended claims.

What is claimed is:

1. A racemic ortho- or parahydroxyarylglycolic acid selected from the group consisting of:
   4-hydroxy 3-tertiobutyl mandelic acid;
   2-hydroxy 5-tertiobutyl mandelic acid;
   2-fluoro 4-hydroxymandelic acid;
   monohydrated 3,5-dimethoxy 4-hydroxy mandelic acid;
   2-hydroxy 5-methyl mandelic acid;
   (1-hydroxy 2-naphthyl) glycolic acid;
   4-ethyl 2-hydroxy mandelic acid, and
   4-hydroxy 3-methyl mandelic acid.

* * * * *